(12) United States Patent
Rezaee et al.

(10) Patent No.: US 9,940,545 B2
(45) Date of Patent: Apr. 10, 2018

(54) METHOD AND APPARATUS FOR DETECTING ANATOMICAL ELEMENTS

(71) Applicant: Change Healthcare LLC, Alpharetta, GA (US)

(72) Inventors: Mahmoud Ramze Rezaee, North Vancouver (CA); Andrew Top, Vancouver (CA); Colin Brown, Vancouver (CA); Ghassan Hamarneh, Vancouver (CA)

(73) Assignee: CHANGE HEALTHCARE LLC, Alpharetta, GA (US)

( * ) Notice: Subject to any disclaimer, the term of this patent is extended or adjusted under 35 U.S.C. 154(b) by 799 days.

(21) Appl. No.: 14/032,791

(22) Filed: Sep. 20, 2013

(65) Prior Publication Data
US 2015/0086091 A1  Mar. 26, 2015

(51) Int. Cl.
*G06K 9/62* (2006.01)
*A61B 5/00* (2006.01)
(Continued)

(52) U.S. Cl.
CPC .......... *G06K 9/6224* (2013.01); *A61B 5/7264* (2013.01); *G06K 9/4614* (2013.01);
(Continued)

(58) Field of Classification Search
CPC .......... G06K 2209/059; G06K 9/6267; G06K 9/6282; G06K 9/4614; G06K 9/6224; G06K 9/6292; A61B 5/7264; G06T 2207/30004; G06T 7/0012; G06T 7/11; G06T 7/143; G06T 2207/20081; G06T 7/12; G06T 7/155
See application file for complete search history.

(56) References Cited

U.S. PATENT DOCUMENTS 5,640,468 A *  6/1997  Hsu .................... G06K 9/00201
                                                     382/190
5,893,085 A *  4/1999  Phillips ................. G01S 7/4802
                                                     706/50

(Continued)

OTHER PUBLICATIONS

Viola et al., *Rapid Object Detection Using a Boosted Cascade of Simple Features*, Computer Vision and Pattern Recognition, vol. 1 (2001) pp. 1-511-1-518.
(Continued)

*Primary Examiner* — Manav Seth
(74) *Attorney, Agent, or Firm* — Alston & Bird LLP

(57) ABSTRACT

A method, apparatus and computer program product are hereby provided to detect anatomical elements in a medical image. In this regard, the method, apparatus, and computer program product may receive a test image and generate a classified image by applying an image classifier to the test image. The image classifier may include at least one decision tree for evaluating at least one pixel value of the test image and the classified image may include a plurality of pixel values. Each pixel value may be associated with a probability that an anatomical element is located at the pixel location. The method, apparatus, and computer program product may also evaluate the classified image using an anatomical model to detect at least one anatomical element within the classified image.

20 Claims, 12 Drawing Sheets

(51) Int. Cl.
*G06T 7/00* (2017.01)
*G06K 9/46* (2006.01)

(52) U.S. Cl.
CPC ......... *G06K 9/6267* (2013.01); *G06K 9/6282* (2013.01); *G06T 7/0012* (2013.01); *G06K 2209/05* (2013.01); *G06T 2207/20081* (2013.01)

(56) References Cited

U.S. PATENT DOCUMENTS

| | | | | |
|---|---|---|---|---|
| 6,614,928 | B1* | 9/2003 | Chung | G01B 11/00 356/627 |
| 6,909,794 | B2* | 6/2005 | Caspi | G06T 3/0068 382/128 |
| 6,944,342 | B1* | 9/2005 | Stahl | G06K 9/6292 382/156 |
| 7,221,787 | B2* | 5/2007 | Luo | G06K 9/38 382/132 |
| 7,308,126 | B2* | 12/2007 | Rogers | G06K 9/3233 128/922 |
| 7,567,707 | B2* | 7/2009 | Willamowski | G06K 9/0061 358/518 |
| 7,574,247 | B2* | 8/2009 | Moreau-Gobard | G06T 7/0012 382/128 |
| 8,073,220 | B2* | 12/2011 | Khamene | G06T 7/149 382/128 |
| 8,078,255 | B2* | 12/2011 | Bhandarkar | G06T 7/0028 382/128 |
| 8,111,923 | B2* | 2/2012 | Csurka | G06K 9/00624 382/170 |
| 8,150,498 | B2* | 4/2012 | Gielen | A61B 5/06 382/128 |
| 8,331,669 | B2* | 12/2012 | Artan | G06T 7/162 382/173 |
| 8,335,364 | B2 | 12/2012 | Osmundson et al. | |
| 8,666,128 | B2* | 3/2014 | Chaney | G06K 9/621 382/128 |
| 8,824,779 | B1* | 9/2014 | Smyth | G06K 9/0061 382/100 |
| 8,878,906 | B2* | 11/2014 | Shotton | H04N 13/0203 348/46 |
| 8,953,856 | B2* | 2/2015 | Ostrovsky-Berman | G06T 7/0032 382/128 |
| 2007/0053589 | A1* | 3/2007 | Gering | G06T 7/0081 382/173 |
| 2008/0117225 | A1 | 5/2008 | Wegenkittl et al. | |
| 2009/0185731 | A1* | 7/2009 | Ray | G06T 7/0012 382/131 |
| 2010/0135554 | A1 | 6/2010 | Kohlmann et al. | |
| 2010/0275145 | A1 | 10/2010 | Nijlunsing et al. | |
| 2015/0043772 | A1* | 2/2015 | Poole | G06K 9/628 382/103 |
| 2015/0065803 | A1* | 3/2015 | Douglas | A61B 1/00009 600/200 |
| 2015/0297313 | A1* | 10/2015 | Reiter | A61B 1/00149 600/408 |

OTHER PUBLICATIONS

Alomari, R. S. et al., *Labeling of Lumbar discs Using both Pixeland Object-Level Features With a Two Level Probabilistic Model*, IEEE TMI, 30(1): (Jan. 2011) 1-10.

Carballido-Gamio, J. et al., *Normalized Cuts in 3D for Spinal MRI Segmentation*, IEEE TMI, 23, No. 1 (Jan. 2004), 36-44.

Criminisi, A. et al., *Regression Forests for Efficient Anatomy Detection and Localization in CT Studies*, in MICCAI 2010 Workshop MCV, LNCS 6533 (2011) 106-117.

Davatzikos, D. et al., *Spatial Normalization of Spine MR Images for Statistical Correlation of Lesions With Clinical Symptoms*, Radiology, 224 (2002) 31 pages.

Felzenszwalb, P. F. et al., *Pictorial Structures for Object Recognition*, IJCV, 61:2005,(2003), 1-42.

Kelm, B. M. et al., *Detection of 3D Spinal Geometry Using Iterated Marginal Space Learning* (2011) 10 pages.

Klinder, T. et al., *Automated Model-based Vertebra Detection, Identification, and Segmentation in CT Images*, Medical Image Analysis 13 (2009) 471-482.

Neubert, A. et al., *Automated 3D Segmentation of Vertebral Bodies and Intervertebral Discs From MRI*, IEEE (2011) 19-24.

Pauly, O. et al., *Fast Multiple Organs Detection and Localization in Whole-Body MR Dixon Sequences*, in MICCAI (2011) 8 pages.

Schmidt, S. et al., *Spine Detection and Labeling Using a Parts-Based Graphical Model*, IPMI 2007, LNCS 4584 (2007) 122-133.

Shen, D. et al., *An Adaptive-Focus Statistical Shape Model for Segmentation and Shape Modeling of 3-D Brain Structures*, IEEE Transactions on Medical Imaging, vol. 20, No. 4, (Apr. 2001) 257-270.

Stern, D. et al., *Automated Detection of Spinal Centrelines, Vertebral Bodies and Intervertebral Discs in Ct and MR Images of Lumbar Spine*, Physics in Medical and Biology 55 (2010) 247-264.

Wels, M. et al., *Multi-Stage Osteolytic Spinal Bone Lesion Detection From CT Data With Internal Sensitivity Control*, SPIE 8315 (Feb. 2012) 8 pages.

Wu, T. et al., *Automated Identification of Thoracolumbar Vertebrae Using Orthogonal Matching Pursuit*, in Proceedings of the Second International Conference on Machine Learning in Medical Imaging, MLMI'11, Berlin, Heidelberg, LNCS 7009 (2011) 126-133.

Zheng, Y. et al., *Four-Chamber Heart Modeling and Automatic Segmentation for 3-D Cardiac CT Volumes* IEEE Transactions on Medical Imaging (2008) 12 pages.

Adeshina, S. et al., *Constructing Part-Based Models for Groupwise Registration*, IEEE International Symposium on Biomedical Imaging; Apr. 14-17, 2010; pp. 1073-1076.

* cited by examiner

METHOD AND APPARATUS FOR DETECTING ANATOMICAL ELEMENTS

TECHNOLOGICAL FIELD

An example embodiment of the present invention relates generally to medical imaging applications, and, more particularly, to a method and apparatus for detecting anatomical elements within a medical image.

BACKGROUND

As medical technology has advanced, it is increasingly common for practitioners to interpret data received from one or more medical imaging devices. Different types of imaging devices (e.g., x-ray images, computed tomography scans, magnetic resonance imaging ("MRI") scans) produce different types of output images, and medical practitioners receive extensive training in performing diagnoses based on these images. However, analysis of these images may involve various time consuming processes, such as manual labeling of elements within an image. For example, a practitioner might spend a significant amount of time manually applying labels to vertebrae in a spinal x-ray or MRI scan in order to report a spinal problem. These manual processes may delay patient results and reduce the availability of the practitioner to perform other tasks. User errors during these processes may result in incorrect or delayed reports. Through applied effort, ingenuity, and innovation, applicant has solved many of these identified problems by developing a solution that is embodied by the present invention, which is described in detail below.

BRIEF SUMMARY

Accordingly, a method, apparatus and computer program product are therefore provided according to an example embodiment of the present invention in order to provide improved detection of anatomical elements within medical images. In this regard, the method, apparatus, and computer program product of an example embodiment may receive a set of training images. The set of training images may be analyzed to generate a classifier. The set of training images may also be used to generate an anatomical model. A test image may be processed using the classifier to determine a set of probabilities associated with locations of anatomical features. The processed test image may then be analyzed using the anatomical model to determine the locations of one or more anatomical features within the image. Embodiments may apply labels to these anatomical features within the test image to assist a practitioner in interpreting the test image.

Embodiments may include a method for detecting anatomical elements. The method may include receiving a test image, generating a classified image by applying an image classifier to the test image. The image classifier may include at least one decision tree for evaluating at least one pixel value of the test image and the classified image comprising a plurality of pixel values. Each pixel value may be associated with a probability that an associated pixel is related to an anatomical element. The method may also include evaluating, using a processor, the classified image using an anatomical model to detect at least one anatomical element within the classified image. The method may also include labeling the detected at least one anatomical element within the test image in response to detecting the at least one anatomical element within the classified image. A location of the anatomical element within the test image may correspond to a location in which the anatomical element was detected within the classified image. The method may also include generating the image classifier by receiving a set of training images. The set of training images may include at least one target image and at least one source image. The method may also include determining at least one image feature, transforming the at least one source image using the at least one image feature to generate at least one feature image, generating at least one decision tree corresponding to the at least one image feature using at least the at least one feature image and the at least one target image, and using the generated at least one decision tree as the image classifier. The method may include generating a plurality of decision trees, each of the decision trees corresponding to a set of image features, evaluating the plurality of decision trees to determine an accuracy value for each decision tree, and selecting at least one of the plurality of decision trees with the highest accuracy value as the image classifier. The at least one image feature may be a Haar-like feature. The at least one decision tree may be generated by a process including determining a set of pixel values associated with a particular node of the decision tree, determining a feature that results in a minimum variance in target pixel values associated with the set of pixel values, and assigning the feature that results in a minimum variance in target pixel values as a decision feature for the particular node of the tree. In some embodiments, the method may include determining a threshold feature value associated with the feature that results in the minimum variance. The threshold feature value may result in a split in the set of pixel values when applied to the set of pixel values. The method may also include assigning the threshold feature value to the particular node of the decision tree. The method may include generating the anatomical model by evaluating a set of anatomical data. The anatomical model may define at least one of a size of an anatomical element, a shape of an anatomical element, or an offset between two or more anatomical elements. In some embodiments, the anatomical elements are spinal vertebrae, and the anatomical model defines an offset between adjacent vertebrae.

Embodiments may also include an apparatus including processing circuitry. The apparatus may be configured to receive a test image, and generate a classified image by applying an image classifier to the test image. The image classifier may include at least one decision tree for evaluating at least one pixel value of the test image. The classified image may include a plurality of pixel values. Each pixel value may be associated with a probability that an associated pixel is related to an anatomical element. The apparatus may also be configured to evaluate the classified image using an anatomical model to detect at least one anatomical element within the classified image. The apparatus may be further configured to label the detected at least one anatomical element within the test image in response to detecting the at least one anatomical element within the classified image. A location of the anatomical element within the test image may correspond to a location in which the anatomical element was detected within the classified image. The apparatus may be further configured to receive a set of training images, the set of training images comprising at least one target image and at least one source image, to determine at least one image feature, to transform the at least one source image using the at least one image feature to generate at least one feature image, to generate at least one decision tree corresponding to the at least one image feature using at least the at least one feature image and the at least one target image, and to use the generated at least one decision tree as the image classifier. The apparatus may be further configured to generate a plurality of decision trees, each of the decision trees corresponding to a set of image features, to evaluate the plurality of decision trees to determine an accuracy value for each decision tree, and to select at least one of the plurality of decision trees with the highest accuracy value as the image classifier. The apparatus may also be configured to determine a set of pixel values associated with a particular node of the decision tree, to determine a feature that results in a minimum variance in target pixel values associated with the set of pixel values, and to assign the feature that results in a minimum variance in target pixel values as a decision feature for the particular node of the tree. In some embodiments, the apparatus may be configured to determine a threshold feature value associated with the feature that results in the minimum variance. The threshold feature value may result in a split in the set of pixel values when applied to the set of pixel value. The apparatus may also be configured to assign the threshold feature value to the particular node of the decision tree. In some embodiments, the anatomical elements are spinal vertebrae, and the anatomical model may define an offset between adjacent vertebrae.

Embodiments may also provide a computer program product comprising at least one non-transitory computer-readable storage medium bearing computer program instructions embodied therein for use with a computer. The computer program instructions may include program instructions configured to receive a test image, to generate a classified image by applying an image classifier to the test image. The image classifier may include at least one decision tree for evaluating at least one pixel value of the test image and the classified image comprising a plurality of pixel values. Each pixel value may be associated with a probability that an associated pixel is related to an anatomical element. The program instructions may also be configured to evaluate the classified image using an anatomical model to detect at least one anatomical element within the classified image.

BRIEF DESCRIPTION OF THE DRAWINGS

Figure 1:
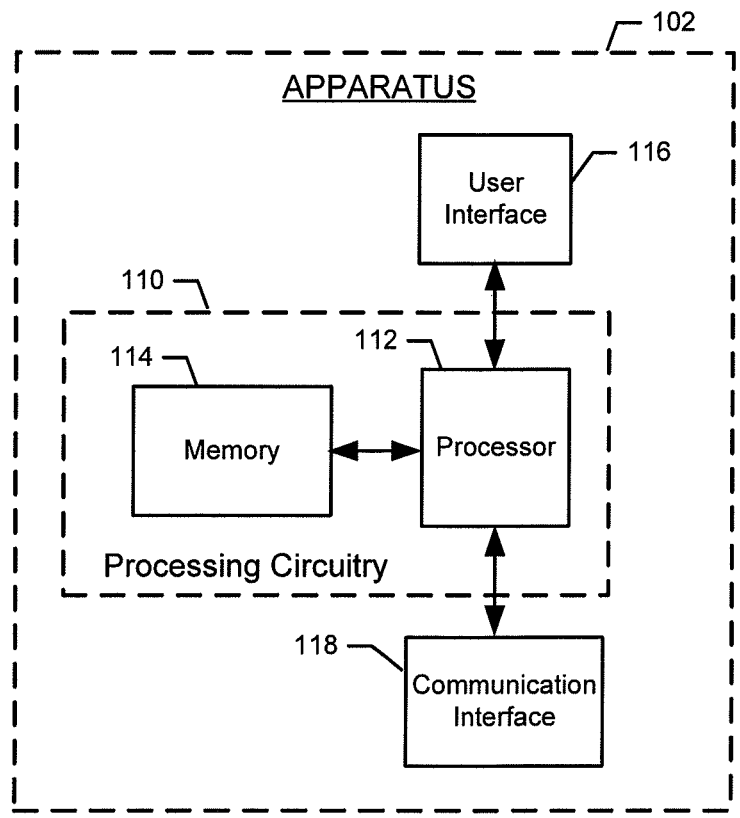
Figure 2:
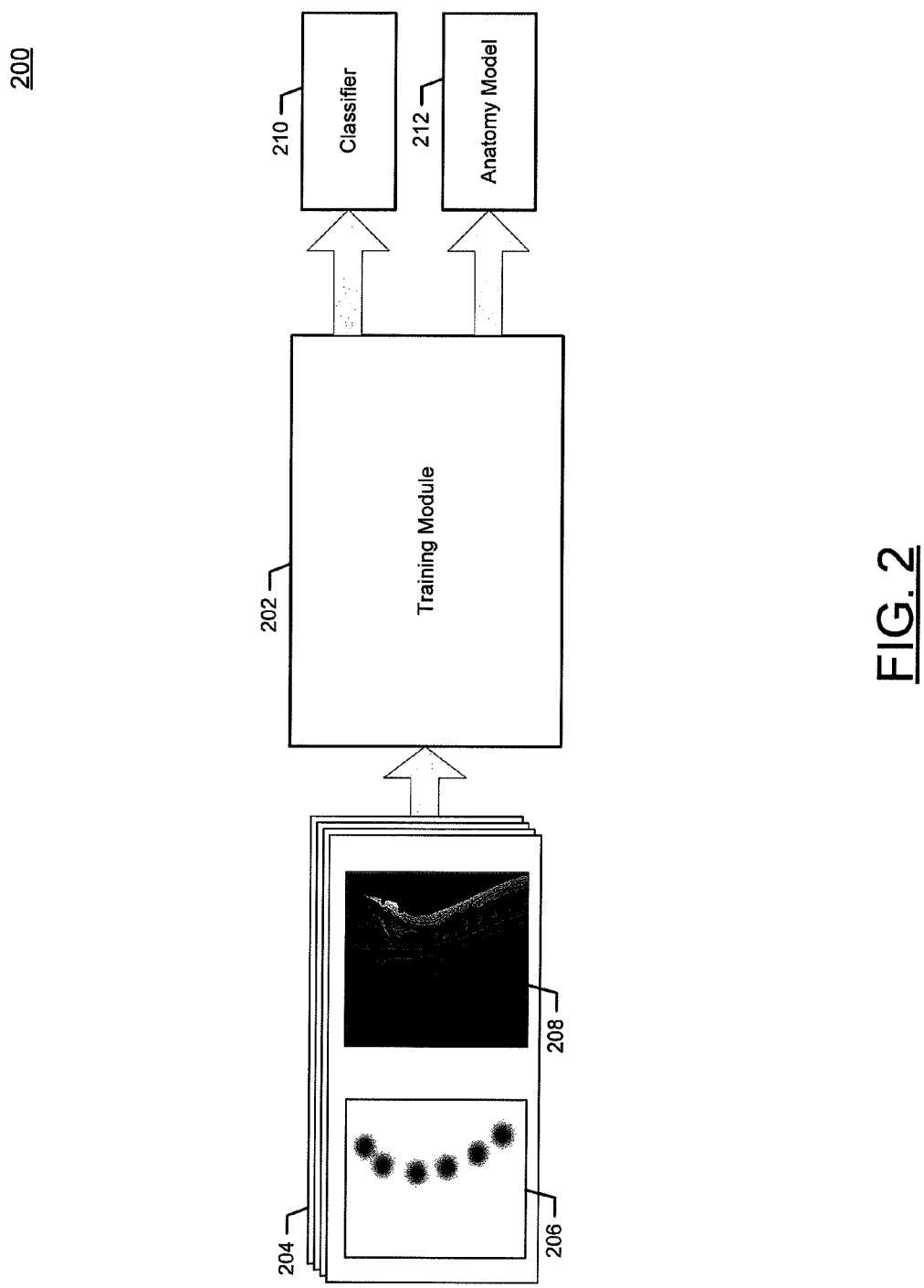
Figure 3:
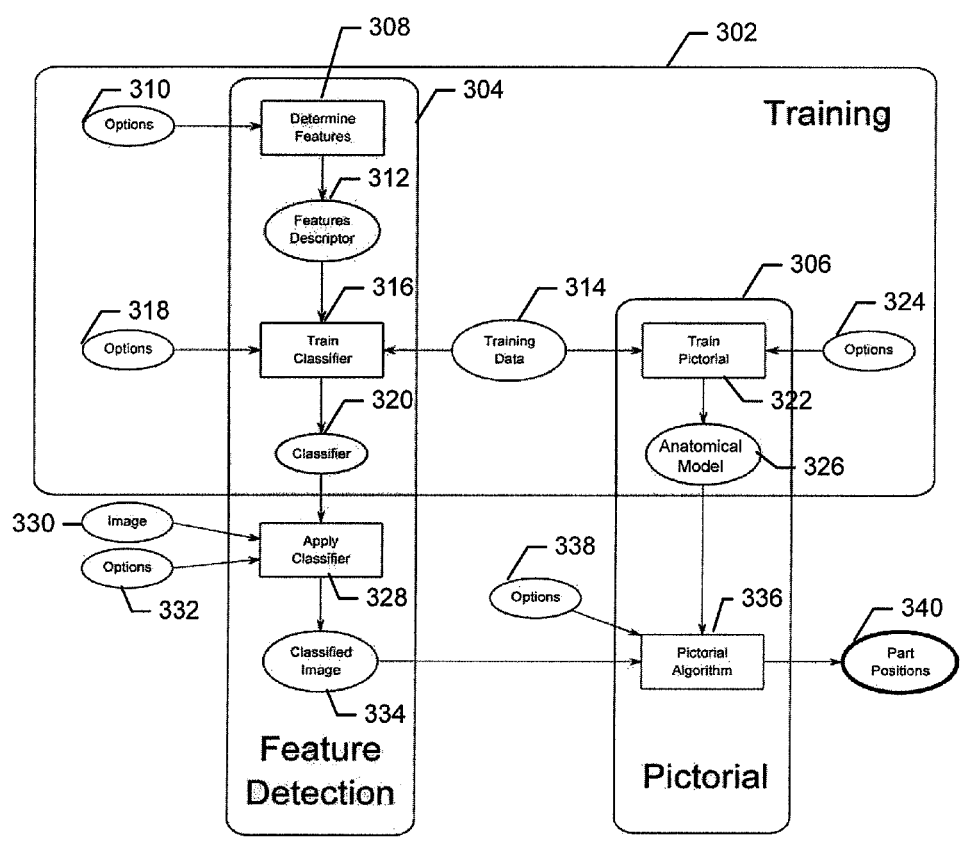
Figure 4:
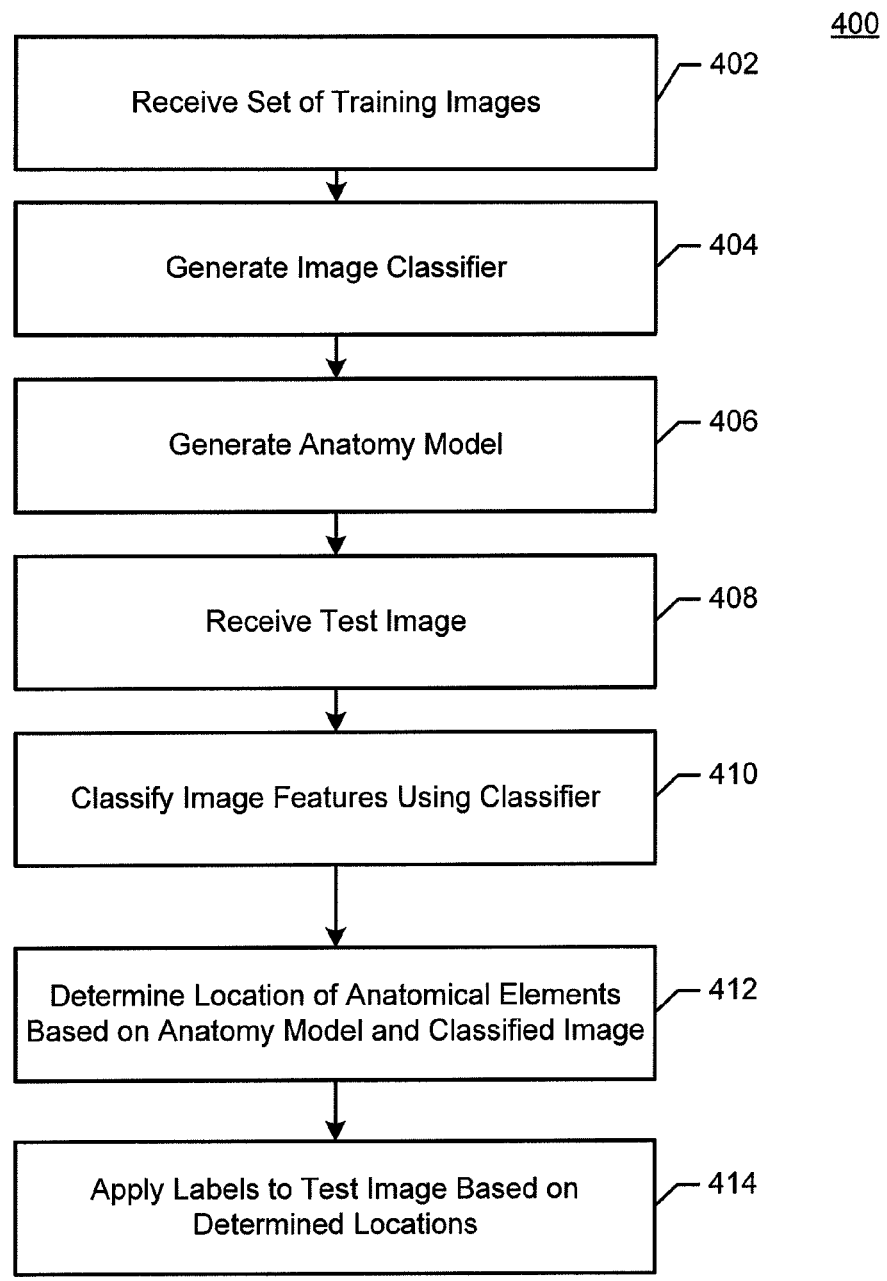
Figure 5:
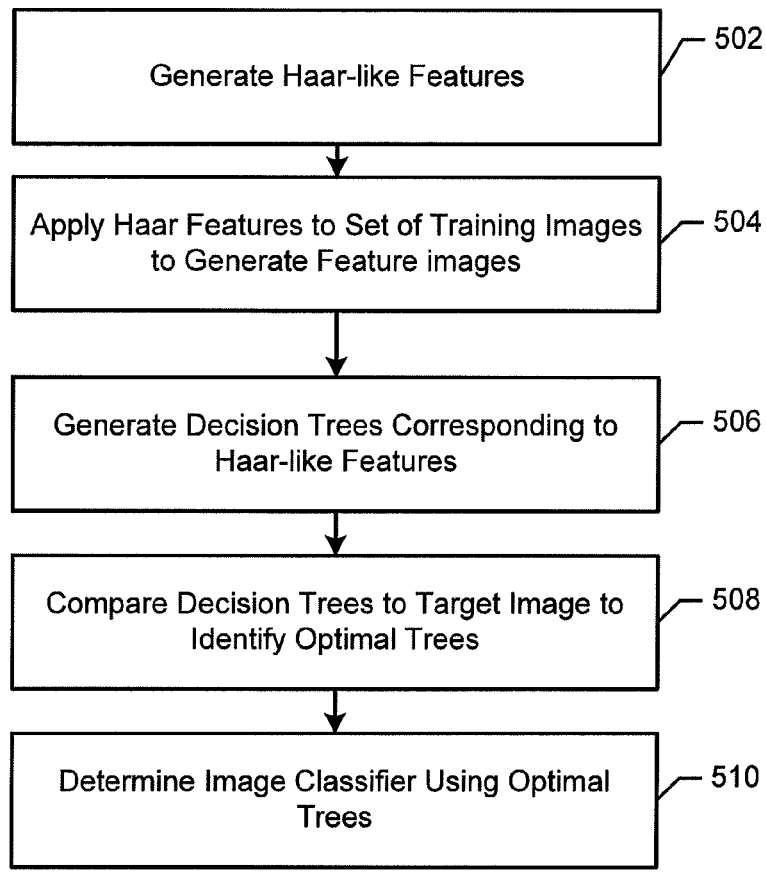
Figure 6:
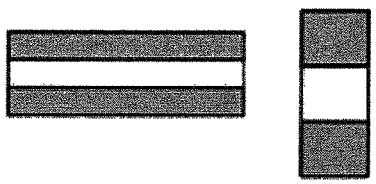
Figure 6:
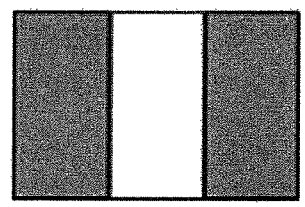
Figure 6:
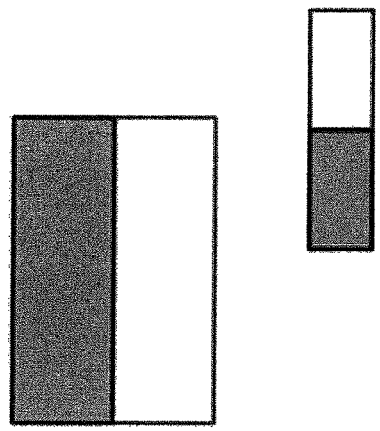
Figure 6:
Figure 7:
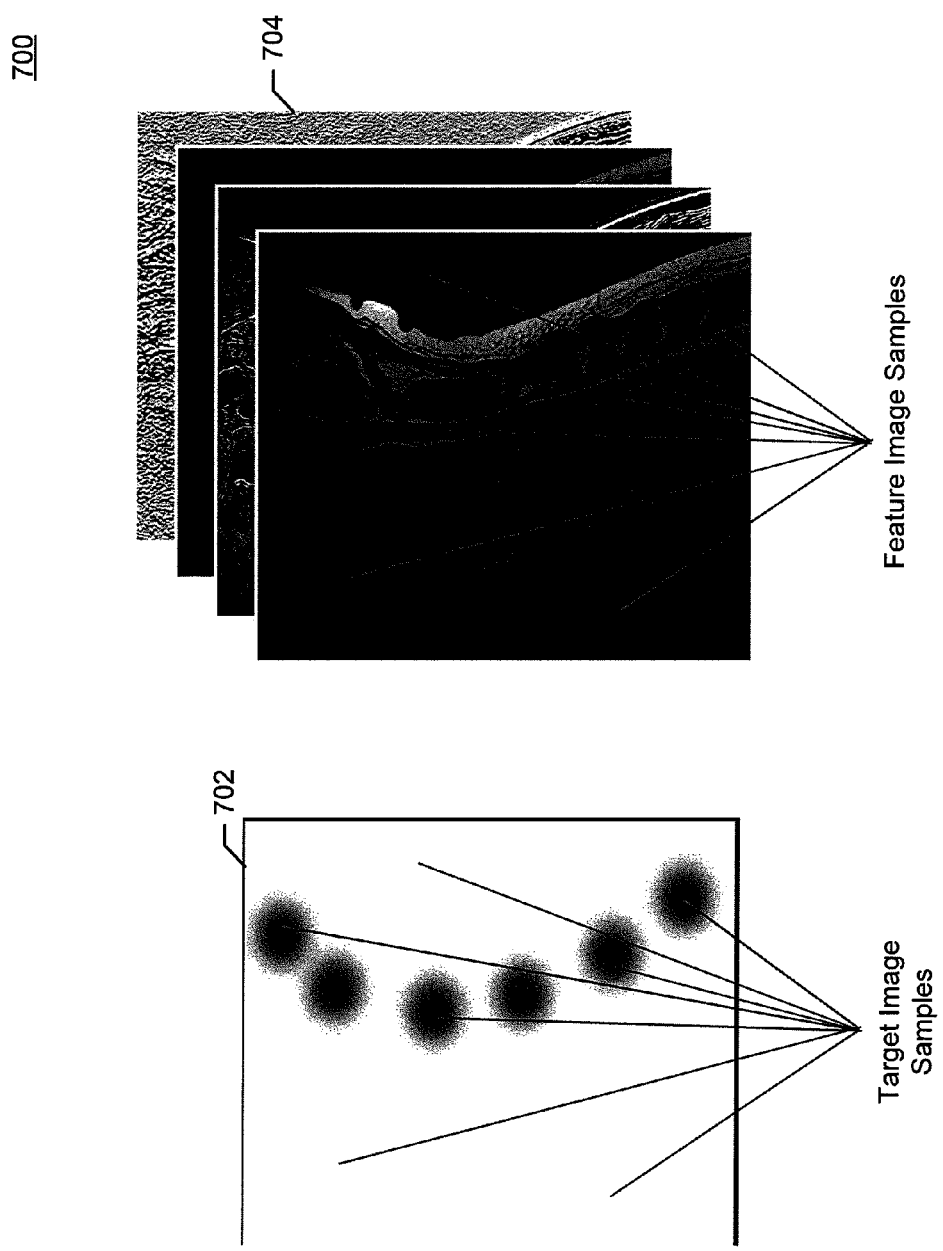
Figure 8:
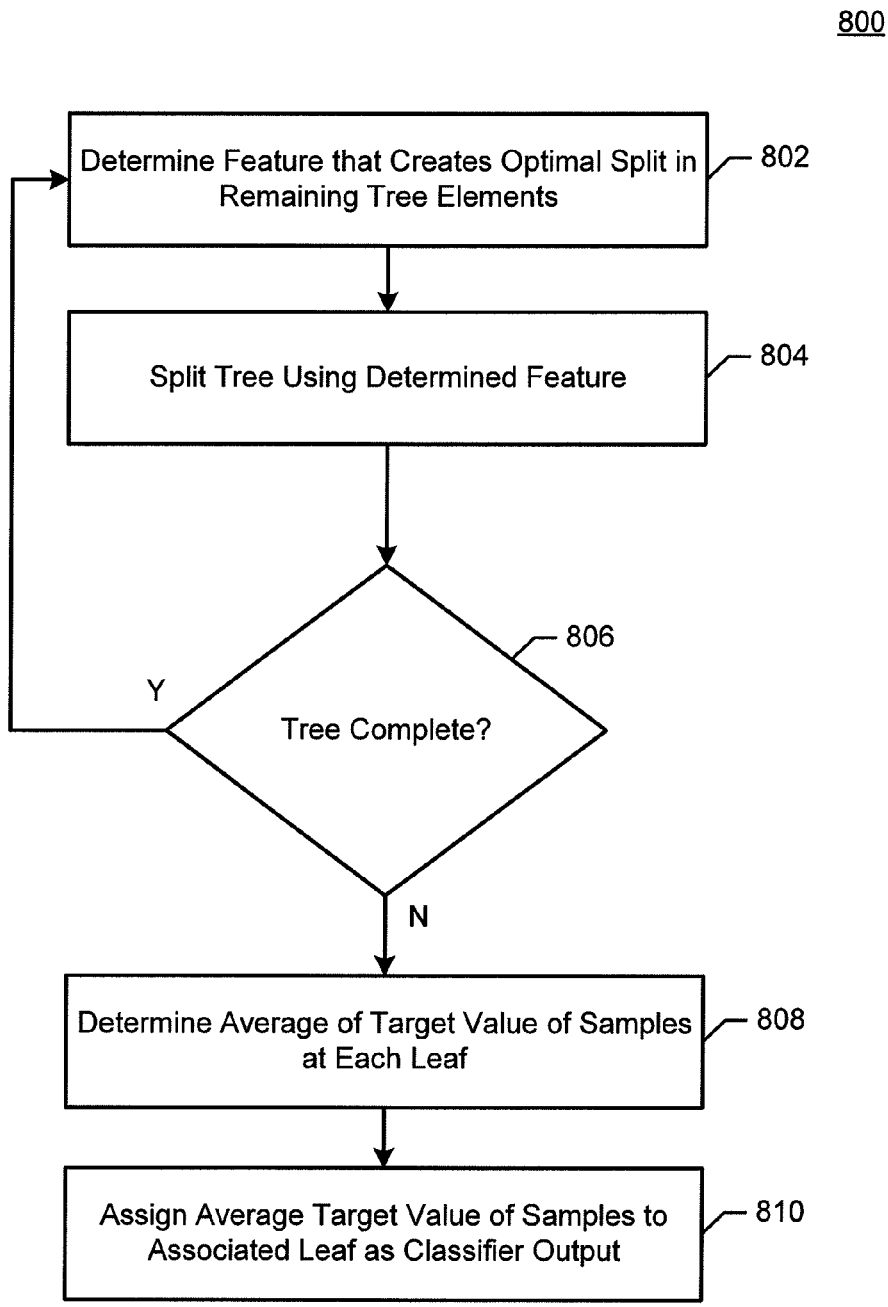
Figure 9:
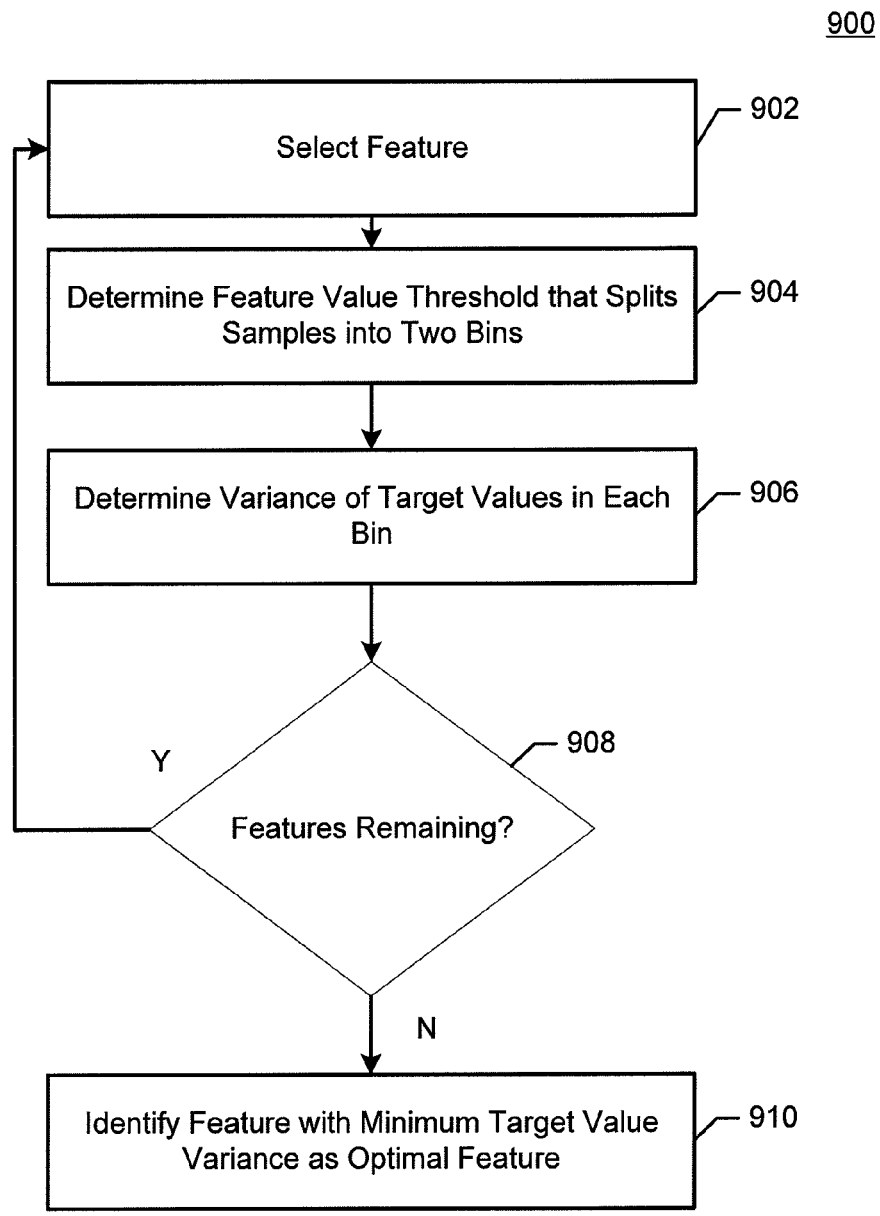
Figure 10:
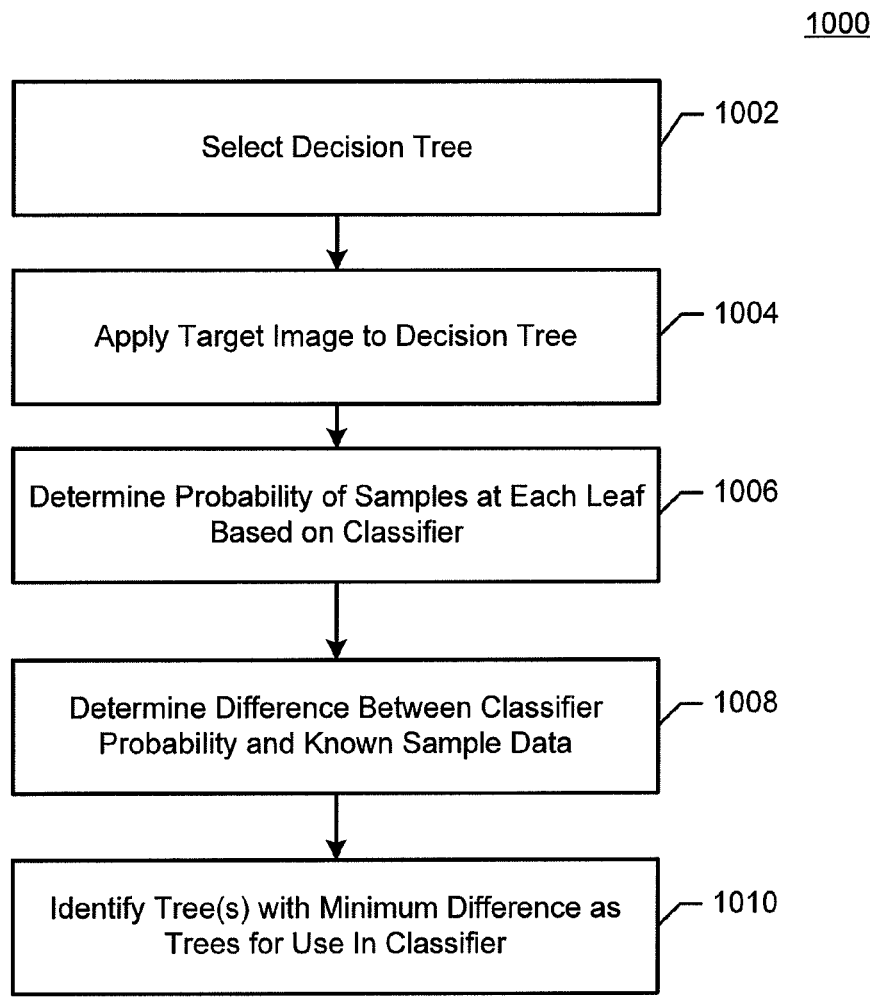
Figure 11:
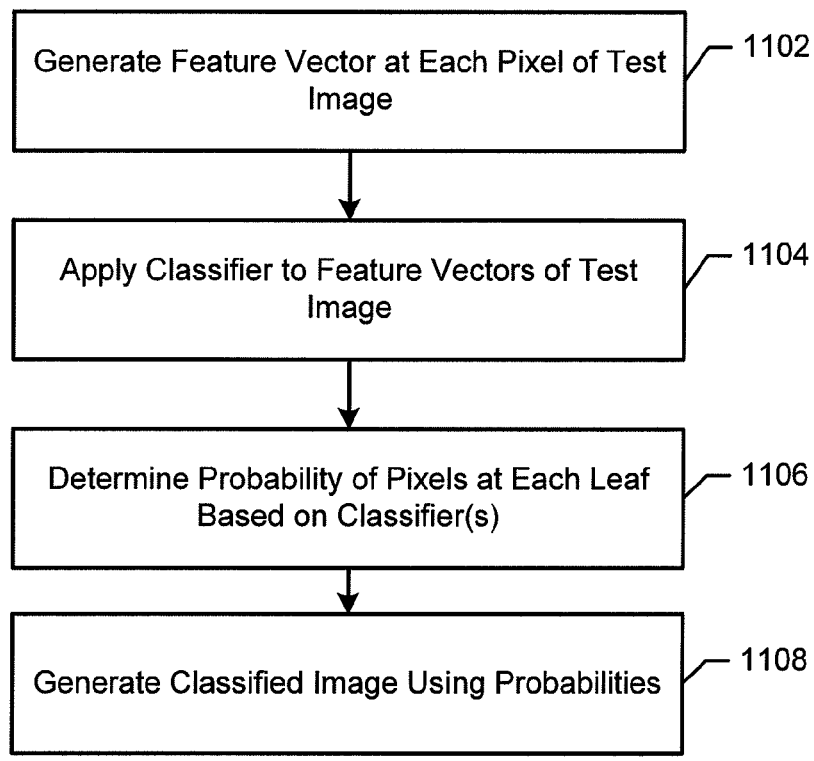
Figure 12:
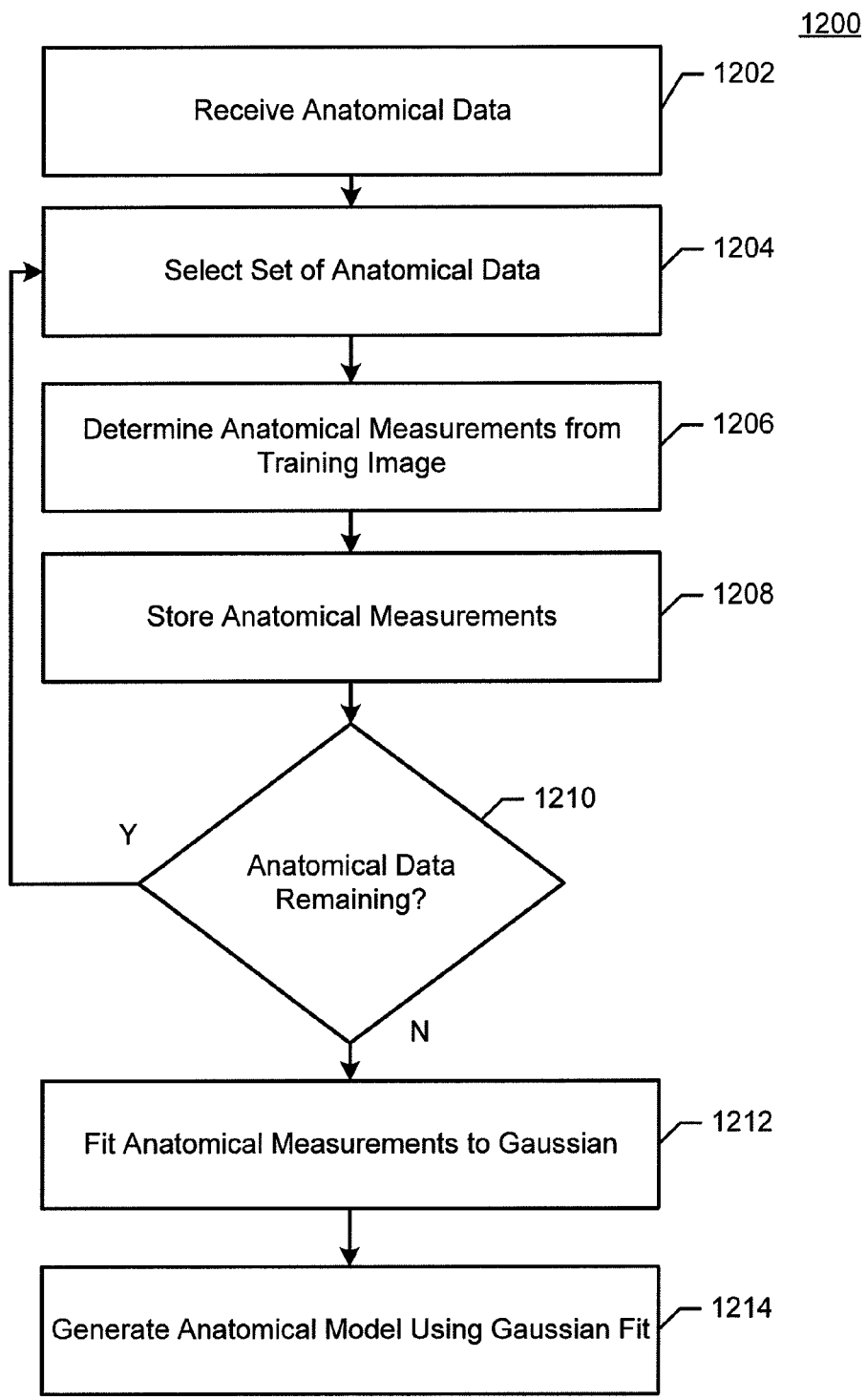

Having thus described certain embodiments of the invention in general terms, reference will now be made to the accompanying drawings, which are not necessarily drawn to scale, and wherein:

FIG. 1 is a block diagram of an apparatus that may be specifically configured in accordance with example embodiments of the present invention;

FIG. 2 is a block diagram of a data flow for generating a classifier and an anatomical model from a set of training images in accordance with example embodiments of the present invention;

FIG. 3 is a block diagram of an overview of an example process for labeling a medical image in accordance with example embodiments of the present invention;

FIG. 4 is a flow diagram of an example method for labeling a medical image in accordance with example embodiments of the present invention;

FIG. 5 is a flow diagram of an example method for determining an image classifier from a set of training images in accordance with example embodiments of the present invention;

FIG. 6 is an illustration of an example set of two dimensional Haar-like features used for determining an image pixel classifier in accordance with example embodiments of the present invention;

FIG. 7 is an illustration of image samples from a set of training images in accordance with example embodiments of the present invention;

FIG. 8 is a flow diagram of an example method for generating a classification tree in accordance with example embodiments of the present invention;

FIG. 9 is a flow diagram of an example method for selecting features for nodes of a classification tree in accordance with example embodiments of the present invention;

FIG. 10 is a flow diagram of an example method for selecting one or more optimal classification trees for use in an image classifier in accordance with example embodiments of the present invention;

FIG. 11 is a flow diagram of an example method for generating a classified image using an image classifier in accordance with example embodiments of the present invention; and FIG. 12 is a flow diagram of an example method for generating an anatomical model in accordance with example embodiments of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Overview

A method, apparatus and computer program product are provided in accordance with an example embodiment of the present invention in order to label medical images. In this regard, a method, apparatus and computer program product of an example embodiment may utilize an image classifier to generate a classified image, where the classified image comprises pixel values representing the probability of the particular pixel belonging to an anatomical element within a test image. The classified image may be analyzed according to an anatomical model to determine a predicted location of the anatomical elements, and the predicted locations may be used to label anatomical elements within the test image.

As used herein, the term "anatomical elements" should be understood to refer to any patient data that can be derived from review of a medical image. For example, anatomical elements should be understood to include, without limitation, organs, nerves, veins, arteries, or any other patient anatomy or function that may be captured using a medical imaging device. It should also be appreciated that the term "anatomical element" may also include elements that, while not part of the patient's body, are still related to patient anatomy and which may be visualized in a medical image. For example, "anatomical elements" should also be understood to include surgical instruments, implants, parasites, injuries, and various other elements that can be discerned and/or diagnosed using medical imaging techniques. In addition, "anatomical elements" should also be understood to represent functional regions, regions of activation, regions of high uptake of X-ray, or the like.

Example Apparatus

FIG. 1 illustrates a block diagram of an apparatus 102 in accordance with some example embodiments. The apparatus 102 may be any computing device capable of receiving a test image and processing the test image to detect one or more anatomical elements. In some particular embodiments, the apparatus 102 may be configured to perform or otherwise assist with medical diagnostic and/or imaging operations. For example, the apparatus 102 may be implemented on a computing device that may be configured to access and display images stored in a Digital Imaging and Communications in Medicine (DICOM) format. Accordingly, it will be appreciated that the apparatus 102 may comprise an apparatus configured to implement and/or otherwise support implementation of various example embodiments described herein.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

The apparatus 102 may include or otherwise be in communication with processing circuitry 110 that is configurable to perform actions in accordance with one or more example embodiments disclosed herein. In this regard, the processing circuitry 110 may be configured to perform and/or control performance of one or more functionalities of the apparatus 102 (e.g., functionalities of a computing device on which the apparatus 102 may be implemented) in accordance with various example embodiments, and thus may provide means for performing functionalities of the apparatus 102 (e.g., functionalities of a computing device on which the apparatus 102 may be implemented) in accordance with various example embodiments. The processing circuitry 110 may be configured to perform data processing, application execution and/or other processing and management services according to one or more example embodiments. In some embodiments, the apparatus 102 or a portion(s) or component(s) thereof, such as the processing circuitry 110, may be embodied as or comprise a chip or chip set. In other words, the apparatus 102 or the processing circuitry 110 may comprise one or more physical packages (e.g., chips) including materials, components and/or wires on a structural assembly (e.g., a baseboard). The apparatus 102 or the processing circuitry 110 may therefore, in some cases, be configured to implement an embodiment of the invention on a single chip or as a single "system on a chip." As such, in some cases, a chip or chipset may constitute means for performing one or more operations for providing the functionalities described herein.

In some example embodiments, the processing circuitry 110 may include a processor 112 and, in some embodiments, such as that illustrated in FIG. 1, may further include memory 114. The processing circuitry 110 may be in communication with or otherwise control a user interface 116 and/or a communication interface 118. As such, the processing circuitry 110 may be embodied as a circuit chip (e.g., an integrated circuit chip) configured (e.g., with hardware, software or a combination of hardware and software) to perform operations described herein.

The processor 112 may be embodied in a number of different ways. For example, the processor 112 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor 112 may comprise a plurality of processors. The plurality of processors may be in operative communication with each other and may be collectively configured to perform one or more functionalities of the apparatus 102 as described herein. The plurality of processors may be embodied on a single computing device or distributed across a plurality of computing devices collectively configured to function as the apparatus 102. In some example embodiments, the processor 112 may be configured to execute instructions stored in the memory 114 or otherwise accessible to the processor 112. As such, whether configured by hardware or by a combination of hardware and software, the processor 112 may represent an entity (e.g., physically embodied in circuitry—in the form of processing circuitry 110) capable of performing operations according to embodiments of the present invention while configured accordingly. Thus, for example, when the processor 112 is embodied as an ASIC, FPGA or the like, the processor 112 may be specifically configured hardware for conducting the operations described herein. Alternatively, as another example, when the processor 112 is embodied as an executor of software instructions, the instructions may specifically configure the processor 112 to perform one or more operations described herein.

In some example embodiments, the memory 114 may include one or more non-transitory memory devices such as, for example, volatile and/or non-volatile memory that may be either fixed or removable. In this regard, the memory 114 may comprise a non-transitory computer-readable storage medium. It will be appreciated that while the memory 114 is illustrated as a single memory, the memory 114 may comprise a plurality of memories. The plurality of memories may be embodied on a single computing device or may be distributed across a plurality of computing devices collectively configured to function as the apparatus 102. The memory 114 may be configured to store information, data, applications, instructions and/or the like for enabling the apparatus 102 to carry out various functions in accordance with one or more example embodiments. For example, the memory 114 may be configured to buffer input data for processing by the processor 112. Additionally or alternatively, the memory 114 may be configured to store instructions for execution by the processor 112. As yet another alternative, the memory 114 may include one or more databases that may store a variety of files, contents or data sets. Among the contents of the memory 114, applications may be stored for execution by the processor 112 in order to carry out the functionality associated with each respective application. In some cases, the memory 114 may be in communication with one or more of the processor 112, user interface 116, or communication interface 118 via a bus or buses for passing information among components of the apparatus 102.

The user interface 116 may be in communication with the processing circuitry 110 to receive an indication of a user input at the user interface 116 and/or to provide an audible, visual, mechanical or other output to the user. As such, the user interface 116 may include, for example, a keyboard, a mouse, a joystick, a display, a touch screen display, a microphone, a speaker, a Light Emitting Diode (LED), a lighting device, an electronic sensor for capturing human body movements, and/or other input/output mechanisms. In embodiments in which the apparatus 102 is implemented on a server, aspects of the user interface 116 may be limited, or the user interface 116 may even be eliminated. For example, the apparatus 102 may act as a server or host device, with a user interface provided by a client application.

The communication interface 118 may include one or more interface mechanisms for enabling communication with other devices and/or networks. In some cases, the communication interface 118 may be any means such as a device or circuitry embodied in either hardware, or a combination of hardware and software that is configured to receive and/or transmit data from/to a network and/or any other device or module in communication with the processing circuitry 110. By way of example, the communication interface 118 may be configured to enable the apparatus 102 to communicate with another computing device via a wireless network, such as a wireless local area network (WLAN), cellular network, and/or the like. Additionally or alternatively, the communication interface 118 may be configured to enable the apparatus 102 to communicate with another computing device via a wireline network. For example, the apparatus 102 may obtain an image of a patient, and label the image with the location of one or more anatomical elements. In some example embodiments, the communication interface 118 may be configured to enable communication between the apparatus 102 and one or more further computing devices via the Internet. Accordingly, the communication interface 118 may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Example Training Set Data Flow

FIG. 2 is a block diagram of a process flow 200 for generating an image classifier and an anatomical model in accordance with example embodiments of the present invention. The process flow 200 may include a training module 202 that receives a set of training images 204. The set of training images 204 may include a plurality of images, including one or more target images 206 and one or more source images 208. The target images 206 represent a mapping of the location of particular anatomical elements to be detected by a generated image classifier. For example, a target image 206 might include data specifying the location of vertebrae in a spinal image. In the present example, the pixels of the target image 206 only display the locations of vertebrae. Each of the target images 206 may be associated with a particular source image 208, representing an image from which the corresponding target image 206 was derived. For example, a target image 206 and source image 208 pair might include a raw MRI scan of a patient spine as the source image 208 and an image containing only the patient's vertebrae as the target image 206. The source image 208 and the target image 206 may be linked together, such that pixel locations within the source image 208 correspond to pixel locations in the target image 206. In some embodiments, the set of training images may include images from multiple viewing angles of the same medical study, allowing a three dimensional analysis to be performed. The set of training images 204 may be used by the training module 202 to generate an image classifier 210. The image classifier 210 may be generated by applying one or more feature detectors to the source image to generate a set of feature images, and processing the feature images to construct a plurality of classification trees. These classification trees may be analyzed to determine which classification trees are optimal for classifying the particular set of training images, and the optimal classification trees may be used as image classifiers in a labeling operation (e.g., voting processes that provide a probabilistic class for the pixels) performed on a test image. Example embodiments for generating and implementing such a classifier are described further below with respect to FIGS. 3-12.

The set of training images 204 may also be used by the training module 202 to generate an anatomical model 212. The anatomical model 212 may include a set of data used to evaluate the locations of anatomical elements in relation to one another. For example, a given set of training data may correspond to medical images of a patient's spine. The anatomical model may examine the known locations of patient vertebrae as identified within the set of training images to generate an anatomical model for the distance between the vertebrae depicted in the set of training images 204. As such, the anatomical model may be used to predict the distance between vertebrae of a sample image. Example methods for utilizing and generating such a model are described further below with respect to FIGS. 3-4 and 12.

Example Labeling Data Flow

Turning now to FIG. 3, an example data flow 300 for labeling anatomical elements within a medical image is depicted. The data flow 300 includes a training phase 302, which includes generating one or more image classifiers and an anatomical model. The image classifier is generated and utilized in a feature detection phase 304, and the anatomical model is generated and utilized in a pictorial phase 306. It should be readily appreciated that, while the training phase 302 is shown as overlapping with portions of the feature detection phase 304 and the pictorial phase 306, the training phase 302 could be decoupled from the use of the image classifier and anatomical model to label medical images. For example, the training phase 302 could be performed as part of a calibration or configuration step at a factory or laboratory, and a set of pre-generated image classifiers and anatomical models could be provided along with sale of a product or device used for labeling of anatomical images. As a specific example, the image classifiers and anatomical models could be included as one or more models or databases in the sale of an electronic medical imaging device (e.g., an MRI machine, a CT scanner, or an image analysis software program). The feature detection phase 304 begins during the training phase 302 at action 308, where a set of features 310 are determined. The set of features 310 may be randomly determined and used for detecting objects within a given image according to various image recognition techniques. For example, the features 310 may be "Haar-like" features, which include adjacent rectangular regions at a specific location in a detection window. Examples of these features are described further below with respect to FIG. 6.

The feature detection phase 304 may receive certain options 310 to configure the feature determination process. For example, the options 310 may include user options that define particular Haar-like features, sets of training data (e.g., selection of a set of training data associated with a particular anatomical feature to be detected or a medical image type to be analyzed) or constraints placed upon the set of training data.

The determined features 310 may be provided to a classifier trainer 316. The classifier trainer 316 may apply the determined features 310 to a set of training data 314, such as described above with respect to FIG. 2. Applying the features to the set of training data 314 may include convolving a feature with a given source image selected from the set of training data to generate a feature image. The source image may be convolved with each of the features to generate a feature vector image associated with the source image. These feature vector images may be used in concert with a target image to generate one or more image classifiers 320 from the set of training data. The process of generating the image classifier(s) 320 may include receiving one or more options 318 to modify the image classifier generation process. For example, the options 318 may indicate which training images should be used, how large the set of training images should be, how large the set of determined features should be, or the like. The options 318 may specify, for example, which anatomy should be treated similarly with respect to particular features, and the depth and number of decision trees utilized during the analysis. In other examples, the options 318 may include a ratio of negative vs. positive targets to sample in training phase (e.g., rather than a completely random sample the analysis may sample all of these pixels and then only a select few 'negative' target pixels when selecting pixels to sample for construction of decision trees), the size of Gaussian used when converting from an anatomical target position (e.g., a labeled vertebrae position) to a target image. Instead of creating a target image by simply putting one 100% probability point at the position of the vertebrae, embodiments may instead mark a fuzzy sphere (created by a Gaussian) around that point. Example embodiments of methods for generating the image classifier 320 are described further below with respect to FIGS. 5-10.

The set of training data 314 may also be employed to generate an anatomical model 326 using a pictorial image evaluation technique during the pictorial phase 306. At operation 322, the set of training data may be analyzed to identify the location of particular anatomical elements. A target image that indicates the location of anatomical elements may be evaluated to determine a relationship between the locations of the anatomical elements. For example, the set of training data may include several images of patient spines with labeled vertebrae, and a model for the vertebrae location may be determined by identifying the position offsets (e.g., the distance between the centers of each vertebra) depicted in the set of training data. An example embodiment for generating an anatomical model is described further below with respect to FIG. 12. The anatomical model generation process may be modified by one or more options 324. For example, the options may specify the type of anatomical data to be modeled, which variables are to be used in the anatomical model, which training images should be used to generate the model, or the like. The options 324 may specify, for example, definitions for the anatomical model, such as which anatomical element positions are linked to and influenced by which other anatomical elements. In some embodiments, training images may be selected by the options 324 as well.

At operation 328, the image classifier 320 may be applied to a test image 330. Applying the classifier may be used to determine the probability that particular pixels within the test image 330 are associated with particular anatomical elements. The output of the image classifier 320 as applied to the test image 330 may include a classified image 334 where the likelihood of a particular anatomical element being located at a particular pixel is represented by a contrast, color, intensity, hue, or other value associated with the pixel, or a neighborhood of the pixel. This classified image 334 may be provided to the pictorial phase 306 for use with the anatomical model 336 to determine the location of one or more anatomical elements. The image classification process 328 may receive and be configured by one or more options 332. For example, the options may include various configurable parameters for modifying an output probability image, such as for smoothing the image to improve spatial regularity and reducing potential false positive results. These options may indicate, for example, the degree of this smoothing process.

At operation 336, the anatomical model is applied to the classified image using a pictorial algorithm. The pictorial algorithm may include the anatomical model to identify anatomical structures within the classified image. For example, an anatomical model that identifies the offsets between spinal vertebrae may be used to detect the shape and location of spinal structures based on the probability distributions within the classified image. In some embodiments the pictorial algorithm may be configured by certain options 338, such as but not limited to selection of a particular anatomical model to be applied. The output of the pictorial algorithm 336 may be a set of labels applied to the test image, indicating the determined location of the anatomical elements or probabilities of anatomical elements belonging in those locations. For example, the pictorial algorithm as described above may label the center of each vertebra in a medical image depicting a patient's spinal column.

Example Flow Diagram for Labeling a Medical Image

Turning now to FIG. 4, an example embodiment of the method 400 for labeling a medical image is described. As described above with respect to FIGS. 2 and 3, the method 400 may serve to first generate an image classifier and an anatomical model from a set of training data, and then apply the image classifier and the anatomical model to a test image to detect and label anatomical features depicted in the test image. In some embodiments, the method 400 may be performed by a processor, such as the processor 112 or an apparatus, such as the apparatus 102.

At action 402, a set of training images are received. As described with respect to FIG. 2, the training images may include a set of target images and a set of source images. The target images may include a set of locations or location probabilities of one or more anatomical elements and the source images may correspond to medical images from which the target images were derived.

At action 404, an image classifier may be generated using the set of training images. For example, one or more features may be applied to each of the source images to generate a set of feature images, and the feature images may be analyzed to determine whether each feature image provides an improved representation of the locations of the anatomical elements by comparing the results of the feature image to the results from other feature images to identify the feature images that best discriminate between parts of the input image. Example methods for generating an image classifier are described in further detail with respect to FIGS. 5-10, below.

At action 406, an anatomy model is generated. The anatomy model may be generated using a set of known locations of anatomical elements. The anatomy model may include a set of location offsets for anatomical elements. For example, the anatomy model may model the size, shape, and/or structure of a set of spinal vertebrae by identifying a distance between certain adjacent vertebrae. The anatomy model may be generated by fitting a curve or function (e.g. a Gaussian) to the set of known locations of anatomy elements.

The set of training images may include one or more images that indicate known locations of anatomical elements for use in generating the anatomy model. Additionally or alternatively, the set of known locations of anatomical elements may be provided in another manner other than as part of the set of training images. For example, a matrix or data table of anatomical elements may be used to generate the anatomy model, such that the anatomy model may be generated without the use of any image analysis techniques. An example of a method for generating the anatomy model is described further below with respect to FIG. 12.

At action 408, a test image (e.g., an image where the locations of anatomical elements are unknown) may be received. The test image may be received directly from an imaging device, via a network connection, as a manual file selection by a user, as part of an electronic communication (e.g., an e-mail), or the like. In some embodiments, the test image may be provided in a certain format (e.g., DICOM), or according to certain other parameters (e.g., certain brightness or contrast settings, a certain viewing angle relative to a patient, or the like).

At action 410, the test image may be classified using the image classifier generated at action 404. The classifier may take the test image as an input and assign each pixel of the test image a probability of being the location of an anatomical element. An example of a method for classifying a test image is described further below with respect to FIG. 11. The output of the classifier may be a classified image, where each pixel of the classified image is associated with a value (e.g., contrast, hue, brightness) representing the likelihood that the particular pixel is the location of an anatomical element (e.g., the darker the pixel, the more likely that pixel is related to an anatomical element).

At action 412, the locations of anatomical elements are derived based on the application of the anatomy model to the classified image. Anatomical elements may be identified by determining a best fit between pixels identified as likely to be related to anatomical elements and the positioning of anatomical elements according to an anatomical model. For example, the anatomy model may define a series of offsets or locations that, relative to one another, define a typical structure for a set of anatomical elements (e.g., an expected location of a next spinal vertebra based on the estimated location of a first spinal vertebra). The anatomy model may be applied to various possible anatomical elements identified within the classified image to identify a set of probable anatomical elements that maximize the probabilities within the classified image while minimizing the error of location calculations derived from the anatomy model.

Various optimization methods may be employed to derive the locations of anatomical elements from the anatomy model and the classified images. For example, in some embodiments, dynamic programming may be employed to determine an optimal set of locations of the anatomical elements using both the anatomy model and the classified image. For example, a dynamic programming algorithm may examine each pixel of a classified image and apply the anatomy model to each pixel to find a set of anatomical element locations that minimizes the deviation from the probabilities of the classified image and the predicted locations based on the anatomy model. In some embodiments, the dynamic programming algorithm may utilize other, non-optimal evaluation methods to increase performance. For example, the algorithm may only examine pixels that have a minimum threshold probability value as possible locations for anatomical elements to be evaluated by the anatomy model. A set of locations within the image that maximize the probability distribution within the classified image while also resulting in a minimum of error for the anatomy model may be identified as the locations of anatomical elements (e.g., the locations of the center of patient vertebra in a spinal image).

At action 414, the set of locations may be labeled on the test image based on the results determined at action 412. For example, upon determination of the locations of the patient's vertebrae, the method may label each vertebra with the name of the vertebra (e.g. L1, L2, L3 for vertebrae of the lumbar spine, C1, C2, C3 for cervical spine, and T1, T2, T3 for thoracic spine). In this manner, the method 400 may function to provide for efficient labeling of anatomical elements within an input image.

Example Methods for Generating and Using an Image Classifier

Turning now to FIGS. 5-11, example embodiments for generating one or more image classifiers from a set of training images and utilizing the generated image classifier in an anatomical element detection operation are described. These Figures illustrate the process by which a set of training images may be analyzed by applying Haar-like features, and generating a decision tree using values for the images derived from the Haar-like features. These decision trees may be evaluated for their accuracy in predicting the location of anatomical elements using a set of target images, and the most accurate decision trees may be selected to be employed as an image classifier.

FIG. 5 illustrates a flow chart of a method 500 by which an image classifier may be generated from a set of training data. As described above, a set of training data may be provided including one or more target images (e.g., an image with the location of certain anatomical features clearly indicated), and one or more source images (e.g., images that have not been processed to directly indicate the location of anatomical features) that correspond to the target images. Generation of a classifier may include identifying one or more features that most clearly identify the anatomical objects within the source images, and using those features to generate a decision tree which may subsequently be used as an image classifier.

At action 502, the method may generate a set of features for use in the classifier. For example, these features may be "Haar-like" features. The term "Haar-like" is used to refer to the use of digital image features that bear similarities to Haar wavelets, and which may include a plurality of rectangles for use in evaluating a set of image pixels. An example of the use of Haar-like features in image analysis techniques is described in Viola and Jones, "Rapid object detection using a boosted cascade of simple features", Computer Vision and Pattern Recognition, 2001. Example Haar-like features are described further below with respect to FIG. 6. The Haar-like features may be generated at random (e.g., by randomly selecting rectangle sizes and types) for each training set. In some embodiments, a different random set of Haar-like features is determined for each target image included in the training set.

In some other embodiments, the Haar-like features may be selected according to particular criteria, or selected in advance by a user. The selected Haar-like features may be selected based on the ability of the particular Haar-like feature to be used to accurately detect the location of a particular anatomical element or element type (e.g., one set of Haar-like features for vertebrae, another for ribs, another for a circulatory system, etc.).

At action 504, the Haar-like features are applied to a set of training images to generate a set of feature images. In some embodiments, the images may be modified or transformed prior to application of the Haar-like features. For example, the images intensity may be adjusted to change the gradient magnitude, to square the image pixel intensities, to take the log of the image intensities, or the like. Application of the Haar-like features to the training images may include performing a set of transforms on the image based on the Haar-like feature. For example, application of the Haar-like feature to a particular pixel or set of pixels may include considering adjacent rectangular regions defined by the Haar-like feature and at a specific location in a detection window, summing up the pixel intensities in each region and calculating the difference between these sums. The Haar-like features may be applied to the training images by convolution, generating an output image for each Haar-like feature that represents the application of the particular Haar-like feature to a particular source image. These feature images may have the intensity of each pixel determined by the convolution of the source image with the Haar-like feature, such that the particular Haar-like feature used to generate the feature image may result in certain elements of the source image being emphasized (e.g., pixel intensity increased) and other elements being deemphasized (e.g., pixel intensity decreased) based on the size, shape, or location of the elements within the image.

At action 506, a decision tree is generated for the set of Haar-like features. The decision tree may be generated by using a set of pixel samples from a target image and a corresponding set of samples from the feature images. These decision trees may include an evaluation of pixel data at particular sample locations. An example of a method for generating a decision tree is described further below with respect to FIG. 8.

At action 508, the generated decision trees are compared to one another to identify one or more optimal decision trees. Different decision trees may have different levels of accuracy due to the different discriminating features (e.g., the Haar-like features described above) with which each tree is generated. Each tree may be generated "optimally" for a given set of features, and the comparison between trees may operate to select an optimal tree from the set of trees. Although each decision at each branch of a particular tree may be considered to be a "weak learner", use of multiple decision points within a tree may result in a good classifier. The use of multiple randomly generated trees may result in a robust "forest" of classifiers that generalizes well to unknown images and is less susceptible to error as a result of noise. Different trees may "vote" for different results for particular pixels, and the output of the forest of trees may be used to derive a probability of membership in a particular class for a particular pixel or pixels. In order to obtain results in an efficient time frame, it may be appropriate to limit the number of decision trees employed by selecting a subset of all generated trees for use in the classifier. As such, action 508 may be employed to identify one or more trees that best match a set of known target data for a given image.

In the present context, the term "optimal" decision tree may refer to a decision tree or set of decision trees that, upon analysis of a target image, generate a set of anatomical element location probabilities most similar to the location of the anatomical elements defined within the target image. Evaluation of the similarity between the results of a particular decision tree and the target image may include evaluating both "negative" results (e.g., where the tree indicates there is a low probability of an anatomical element) and "positive" results (e.g., where the tree indicates that there is a high probability of an anatomical element). In this regard, evaluation of the decision tree may include not only maximizing a detection rate (e.g., ensuring that the tree finds each anatomical element), but also minimizing a false positive rate (e.g., ensuring that the tree does not indicate a high probability of an anatomical element in a location where no anatomical element exists).

For example, decision trees may be selected to minimize the amount of error between a calculated location probability determined using the tree and a known set of anatomical element locations identified in a target image. An example of a method for evaluating a set of decision trees to determine optimal trees is described further below with respect to FIG. 10.

At action 510, an image classifier is generated using the selected optimal trees. The selected optimal decision trees may be used to process pixels of a test image, and a probability value may be assigned to each pixel of the test image based on which leaf of each tree the pixel is assigned during the processing operation. An example of a method for evaluating a test image using a decision tree is described further below with respect to FIG. 11. It should be appreciated that various elements of the method 500 may be repeated in order to generate a plurality of decision trees for use in the classifier. For example, different decision trees that correspond to different sets of Haar-like features (e.g., different randomly generated sets) may be generated and evaluated for inclusion in the classifier.

Turning now to FIG. 6, an example set of 2-D Haar-like features are described. As described above, Haar-like features may include a set of two or more rectangles for use in detecting objects within an image, with each rectangle representing a value such as −1 or 1. The Haar-like features may be convolved or slid across an image to produce a new convolved image. Given a simple rectangular Haar-like feature as depicted in FIG. 6, a pixel in the convolved image may be defined as the difference of the sum of pixels of areas inside each rectangle, which can be at any position and scale within the original image. This feature set is called 2-rectangle features. Haar-like features may also include 3-rectangle features and 4-rectangle features. The values resulting from application of a Haar-like feature to an image may indicate certain characteristics of a particular area of the image. Each feature type can indicate the existence (or absence) of certain characteristics in the image, such as edges or changes in texture. For example, a 2-rectangle feature can indicate where the border lies between a dark region and a light region.

FIG. 7 depicts an image sampling process 700 for generating an image classifier in accordance with some example embodiments. After generating the feature images as described above with respect to FIG. 5, embodiments may evaluate each feature image as compared to a known set of anatomical element locations provided in a target image. This evaluation may be performed by identifying pixel values at particular pixels of the target image and the corresponding pixel values in each feature image. A plurality of pixels may be selected from a target image 702. These pixels may be selected at random, or they may be selected to obtain a certain sample distribution within the target image. These selected pixels may correspond to the same pixel location in each of the feature images 704 generated by applying a Haar-like feature to a source image. In this manner, the samples may line up such that if a pixel at coordinates (100, 134) is sampled in the target image, the same pixel at coordinates (100, 134) of each feature image may also be sampled. These sampled pixel values may be utilized to generate a decision tree and to evaluate the generated decision tree as described further below with respect to FIGS. 8-10.

FIG. 8 depicts a flow chart illustrating an example of a method for generating a decision tree using a set of feature images. As described above, image features may be applied to a set of source images to generate a set of feature images. Each source image may generate a plurality of feature images, with each feature image associated with one of a set of features (e.g., the Haar-like features) as described above. This set of feature images may be evaluated together to generate a decision tree for use in evaluating other images. In particular, pixel values associated with particular pixel coordinates of each of the set of feature images may be utilized to build the decision tree.

At action 802, a feature is determined that creates an optimal split in any remaining elements of the tree, such as a set of pixel sample values associated with the set of feature images. The optimal split may be based upon characteristics of each pixel at a pixel sample location within the feature image, and how those pixel characteristics relate to characteristics of pixels at the same location in the target image. An example embodiment for determining a feature that results in an optimal split is described further below with respect to FIG. 9.

At action 804, the tree is split using the feature determined at action 804. Splitting of the tree may refer to placing pixels with pixel values that are below a threshold defined for the feature on one leaf of a node, and pixels with pixel values that are greater than the threshold on another leaf of the same node, thereby splitting the set of pixels into the two leaf nodes based on the threshold.

At action 806, the tree may be evaluated to determine if the tree is complete. For example, the tree may have a defined depth, and the tree may be considered complete when the defined depth has been reached. Additionally or alternatively, the tree may be considered complete when no more pixels may be split (e.g., only one pixel remains at each leaf node). Embodiments may allow the use of the same feature at more than one decision point in the tree, as the same feature may give the best discrimination between more than one set of pixels, or a subset of the same group of pixels. If the tree is not complete, the method may return to action 802 to recursively evaluate the pixels of each leaf node to determine an optimal feature for splitting the set of pixels in the new leaf node. Otherwise, the method proceeds to action 808.

At action 808, the pixel values of the target image corresponding to the pixels at each leaf node are evaluated to determine a probability to be associated with that leaf. For example, the intensities of the target image pixels associated with the pixels of the particular leaf node may be averaged, such that if an intensity of 0.1 indicates a 10% probability of the presence of an anatomical element, an intensity of 0.5 indicates a 50% probability, and an intensity of 0.9 indicates a 90% probability, the probability assigned to a leaf node containing pixels corresponding to target image pixels with the values of [0.25, 0.5, 0.75, 0.9] would be 60%. This probability represents the probability that a pixel that is assigned to that particular leaf during an image classification process contains an anatomical element. At action 810, the determined probability is assigned to the particular leaf. It should be appreciated that the method 800 may be performed recursively to fill out the entire decision tree, including assigning a probability to each leaf node of the tree. The tree may then be evaluated for accuracy as described further below to FIG. 10.

Turning now to FIG. 9, an example of a method 900 for determining an optimal feature for splitting a decision tree is described. As described with respect to FIG. 8, a decision tree may be generated by comparing pixel values associated with samples taken from a feature image with samples taken from a target image to determine if the feature does an acceptable job of separating pixels that are related to anatomical elements from pixels that are not related to anatomical elements. The method 900 describes a process by which particular features can be evaluated for accuracy and inclusion in a decision tree.

At action 902, a feature is selected for evaluation to determine how well the feature splits a set of sample pixel values. As described above, the feature may be associated with a particular feature image derived by applying a Haar-like feature to a particular source image. Each feature may also be associated with a particular set of pixel sample values derived from sampling of the feature image associated with the feature. For example, if 11 pixel samples are taken, then each feature may be associated with an 11 value pixel vector corresponding to the intensity of those particular pixels in the associated feature image. As such, each feature image may be associated with a different set of pixel values, owing to the different transforms performed on each feature image (e.g., different Haar-like feature used in convolution).

At action 904, a threshold is determined that splits the set of pixel samples associated with the image into two bins. For example, the threshold may be chosen such that an equal number of pixels have a greater intensity and a lesser intensity than the threshold, splitting the set of pixels into two groups. It should be readily appreciated that the groups may not be equal. Since each feature may have a different set of associated pixel values, each feature may also have a separate threshold used for separating the associated pixel values into two groups.

At action 906, the values of the samples associated with the target image are determined for each group, and a variance is determined for the set of target values. In other words, instead of using the pixel values for the feature image, the pixel values of the associated pixels from the target image are used, since these values represent the actual known location of anatomical elements. As such, the threshold determination step of action 904 is used to separate the pixels into two groups using the values associated with the feature image, while the variance of the pixel values of the separated groups is determined using the pixel values of the target image. In this manner, the validity of splitting based on the particular feature may be identified by comparing the pixel group classification with known data from the target image, such that a low variance on each side of the split indicates a better split, while a high variance indicates a sub-optimal split.

At action 908, the method determines whether any features are left to be evaluated for the set of pixels. If so, the method returns to action 902 to determine a variance score for the next feature. Otherwise, the method proceeds to action 910 to evaluate the features based on the determined variances.

At action 910, the feature that resulted in the split with the lowest target value variance is identified as the optimal feature for splitting the set of sample pixels. It should be readily appreciated that the method 900 may be repeated numerous times during creation of a decision tree, in order to select a feature that results in an optimal split at each node of the tree.

Turning now to FIG. 10, an example method 1000 is described for evaluating the accuracy of one or more decision trees and generating an image classifier based on the accuracy evaluation. As described above, embodiments may result in the generation of multiple decision trees. These decision trees may be evaluated against sample data from a known target image or images to determine how close the predicted probability for each decision tree is to known anatomical element location data provided in the target samples.

At action 1002, the method 1000 may begin by selecting a decision tree, such as one of the decision trees generated by the method 800 described above. At action 1004, a target image, in which the location of depicted anatomical elements is known a priori, may be applied to the decision tree. For example, sample pixel values may be determined for particular pixel coordinates within the target image. These sample pixel values may be evaluated using the decision tree, such that each pixel is assigned to a leaf of the decision tree (e.g., moving down the tree to a leaf based on where the pixel value falls in relation to a threshold). In order to evaluate each sample pixel using a particular feature, application of the target image to the decision tree may include generating a feature vector for each sample pixel, where the feature vector defines how the particular sample pixel would be modified if the target image were transformed using each particular feature. Evaluation of nodes in the tree may include using the term of the feature vector corresponding to the feature associated with the particular node. In other words, the determination as to whether a particular pixel is greater than or less than a particular feature threshold value may be determined using a pixel value resulting from a transform of the target image sample pixel with the particular Haar-like feature associated with the particular evaluation node of the tree.

Once each of the sample pixels has been assigned to a leaf of the tree, at action 1006 a probability may be determined for each of the sample pixel values based on the leaf to which the value is assigned. For example, as described above with respect to FIG. 8, each of the leaves of the tree may be associated with a particular probability derived when the tree is constructed. At action 1008, a difference is determined between the probability determined based on the classifier and known data associated with the sample. For example, if the leaf of the decision tree indicates that a particular pixel has a 90% probability of being associated with an anatomical element location, but the known sample data indicates that there is no anatomical element at the location of the particular pixel, then the results provided by the decision tree may be suspect. Similarly, if the decision tree indicates a low probability that a particular pixel has an anatomical element, but the known data indicates an anatomical element is located at that pixel, then this may indicate that the decision tree is suspect or otherwise not providing quality results. Many such pixels may be evaluated for each decision tree, as a certain number of "misses" or "false positives" may be expected, and decision trees may be evaluated based on an aggregate of results (e.g., an overall accuracy rate over 10, 50, 100, or 1000 pixel evaluations).

At action 1012, one or more trees with a minimum difference between the classifier probability and known data (e.g., a highest accuracy rate) may be selected for inclusion in a classifier used to identify anatomical element locations in test images. For example, four classifiers may be selected based on the four decision trees with the highest accuracy.

Turning now to FIG. 11, an example embodiment is provided for applying a classifier to a test image to assist with detection of anatomical elements within the test image. As described above, a classifier may include one or more decision trees generated using a set of training data, as described above with respect to FIGS. 5-10. This classifier may be applied to a test image to determine a probability that an anatomical element is located at each pixel of the image. These probabilities may be used to generate a classified image, with pixel values of the classified image each corresponding to a particular probability (e.g., intensity or contrast values of each pixel associated with the probability). This classified image may be used in conjunction with an anatomical model to identify one or more anatomical elements within the test image.

At action 1102, a feature vector is generated for each pixel of the test image. The feature vector may correspond to each feature associated with a particular classifier being applied to the test image to determine the impact of the feature on a pixel value for each pixel of the image. Although the instant embodiment is described with respect to utilizing each pixel of the image, it should be appreciated that certain subsets of the pixels may also be employed according to various methods for selecting certain sets of pixels. For example, a reduced set of pixels (e.g., every other pixel) may be analyzed to reduce processor load.

At action 1104, the feature vectors are used to apply the classifier to the test image. For example, if the classifier includes a set of four decision trees, each pixel vector may be fed through each tree to determine to which leaf of the tree the pixel vectors is assigned. The resulting four values (one value for each leaf of one of the four classification trees) may be combined (e.g., averaged) to determine an output value for each pixel. This process may be repeated by analyzing each pixel vector using the one or more decision trees contained in the classifier.

At action 1106, the pixel values for each pixel vector may be used to generate a classified image. For example, each pixel value (e.g., an intensity of each pixel) of the classified image may correspond to the probability that the particular pixel is associated with an anatomical element, as determined by the decision trees of the classifier. This classified image may be provided to an anatomical model for evaluation to determine the location of anatomical elements within the original test image.

Example Method for Generating an Anatomical Model

Turning now to FIG. 12, an example embodiment for generating an anatomical model is described. As described above, an anatomical model may be generated for use in conjunction with an image classifier to detect the location of one or more anatomical elements in a test image. Generation of the anatomical model may be performed using pictorial image evaluation techniques, where the location of particular anatomical elements are derived from known data and a model is generated describing the relationship between these anatomical elements. This model may be used to describe the size, shape, structure, form, location, and the like of the anatomical elements.

At action 1202, a set of anatomical data may be received. As described above with respect to FIG. 4, the set of anatomical data may include a set of training images that are presented as a set of target images and a set of source images. In some additional or alternative embodiments, the anatomical model may also be generated using expert knowledge about a particular anatomical structure (e.g., based on physiological structure models developed by medical practitioners) to supplement or replace the set of training images. However, the set of anatomical data may additionally or alternatively not include image content. For example, instead of providing an image or set of images, the anatomical data may include raw data indicating various characteristics of known anatomical data such as offsets, measurements, direction vectors between elements, or the like. As such, it should be readily appreciated that an anatomical model could be generated according to the embodiments described herein without reference to any image data, instead relying upon non-image anatomical data.

At action 1204, a next set of anatomical data is selected for evaluation. For example, a next image of a set of image training data may be selected, or a next row in an anatomical data table may be selected for evaluation. At action 1206, a set of anatomical measurements are determined from the selected anatomical data. For example, the anatomical data may be evaluated to determine a set of offsets between two anatomical elements (e.g., between two adjacent vertebrae). Various other measurements may also be employed, such as size (e.g., width of veins and arteries), shape (e.g., shape of a particular organ), and the like as described above. At action 1208, the anatomical measurements may be stored for later use in generation of an anatomical model.

At action 1210, a determination is made as to whether any anatomical data remains for evaluation. If so, the method returns to action 1204 to evaluate the next set of anatomical data, otherwise the method proceeds to action 1212 to proceed with generation of the anatomical model.

At action 1212, the method may fit the stored anatomical measurements to a model. For example, the method may fit a Gaussian to the anatomical relative offset measurements. The anatomical model may be generated for the particular set of anatomical data based on the fit to the model. The anatomical model may later be applied during an anatomical element detection process to determine a best fit of a set of probabilities related to a classified image. As described above with respect to FIG. 4, anatomical elements may be identified based on minimizing an error from the anatomical model while maximizing the probabilities determined by the classified image.

It will be understood that each block of the flowcharts, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 104 of an apparatus employing an embodiment of the present invention and executed by a processor 102 of the apparatus. In some embodiments, portions of the various methods may be facilitated by a user instead of, in addition to, or in conjunction with an algorithm. For example, a user may interactively choose features for a decision tree, decide which tests are utilized at particular branches of a decision tree, decide a class for a particular pixel, or the like.

As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for detecting anatomical elements comprising:

receiving a test image;
generating one or more feature vectors, wherein generating each feature vector comprises convolving a respective feature with the test image;
generating a classified image by using the one or more feature vectors to apply an image classifier to the test image, the image classifier comprising at least one decision tree, wherein application of the image classifier to the test image comprises feeding the one or more feature vectors through the at least one decision tree to generate at least one pixel value of the test image, the classified image comprising a plurality of pixel values, wherein generation of each pixel value assigns the pixel value a probability that its associated pixel is related to an anatomical element; and
evaluating, using a processor, the classified image using an anatomical model to detect at least one anatomical element within the classified image.

2. The method of claim 1, further comprising labeling the detected at least one anatomical element within the test image in response to detecting the at least one anatomical element within the classified image.

3. The method of claim 2, wherein a location of the at least one anatomical element within the test image corresponds to a location in which the at least one anatomical element was detected within the classified image.

4. The method of claim 1, further comprising generating the image classifier by:
receiving a set of training images, the set of training images comprising at least one target image and at least one source image;
determining at least one image feature;
transforming the at least one source image using the at least one image feature to generate at least one feature image;
generating at least one decision tree corresponding to the at least one image feature using at least the at least one feature image and the at least one target image; and
using the generated at least one decision tree as the image classifier.

5. The method of claim 4, further comprising:
generating a plurality of decision trees, each of the decision trees corresponding to a set of image features;
evaluating the plurality of decision trees to determine an accuracy value for each decision tree; and
selecting at least one of the plurality of decision trees with the highest accuracy value as the image classifier.

6. The method of claim 4, wherein the at least one image feature is a Haar-like feature.

7. The method of claim 4, wherein the at least one decision tree is generated by a process comprising:
determining a set of pixel values associated with a particular node of the decision tree;
determining a feature that results in a minimum variance in target pixel values associated with the set of pixel values; and
assigning the feature that results in a minimum variance in target pixel values as a decision feature for the particular node of the tree.

8. The method of claim 7, further comprising:
determining a threshold feature value associated with the feature that results in the minimum variance, wherein the threshold feature value results in a split in the set of pixel values when applied to the set of pixel values; and
assigning the threshold feature value to the particular node of the decision tree.

9. The method of claim 1, further comprising generating the anatomical model by evaluating a set of anatomical data.

10. The method of claim 1, wherein the anatomical model defines at least one of a size of an anatomical element, a shape of an anatomical element, or an offset between two or more anatomical elements.

11. The method of claim 1, wherein the anatomical elements are spinal vertebrae, and wherein the anatomical model defines an offset between adjacent vertebrae.

12. An apparatus comprising processing circuitry configured to:
receive a test image;
generate one or more feature vectors, wherein generating each feature vector comprises convolving a respective feature with the test image;
generate a classified image by using the one or more feature vectors to apply an image classifier to the test image, the image classifier comprising at least one decision tree, wherein application of the image classifier to the test image comprises feeding the one or more feature vectors through the at least one decision tree to generate at least one pixel value of the test image, the classified image comprising a plurality of pixel values, wherein generation of each pixel value assigns the pixel value a probability that its associated pixel is related to an anatomical element; and
evaluate the classified image using an anatomical model to detect at least one anatomical element within the classified image.

13. The apparatus of claim 12, further configured to label the detected at least one anatomical element within the test image in response to detecting the at least one anatomical element within the classified image.

14. The apparatus of claim 13, wherein a location of the at least one anatomical element within the test image corresponds to a location in which the at least one anatomical element was detected within the classified image.

15. The apparatus of claim 12, further configured to:
receive a set of training images, the set of training images comprising at least one target image and at least one source image;
determine at least one image feature;
transform the at least one source image using the at least one image feature to generate at least one feature image;
generate at least one decision tree corresponding to the at least one image feature using at least the at least one feature image and the at least one target image; and
use the generated at least one decision tree as the image classifier.

16. The apparatus of claim 15, further configured to:
generate a plurality of decision trees, each of the decision trees corresponding to a set of image features;
evaluate the plurality of decision trees to determine an accuracy value for each decision tree; and
select at least one of the plurality of decision trees with the highest accuracy value as the image classifier.

17. The apparatus of claim 15, wherein apparatus is further configured to:
determine a set of pixel values associated with a particular node of the decision tree;
determine a feature that results in a minimum variance in target pixel values associated with the set of pixel values; and
assign the feature that results in a minimum variance in target pixel values as a decision feature for the particular node of the tree.

18. The apparatus of claim 17, further configured to:

determine a threshold feature value associated with the feature that results in the minimum variance, wherein the threshold feature value results in a split in the set of pixel values when applied to the set of pixel values; and assign the threshold feature value to the particular node of the decision tree.

19. The apparatus of claim 12, wherein the anatomical elements are spinal vertebrae, and wherein the anatomical model defines an offset between adjacent vertebrae.

20. A computer program product comprising at least one non-transitory computer-readable storage medium bearing computer program instructions embodied therein for use with a computer, the computer program instructions comprising program instructions configured to:

receive a test image;

generate one or more feature vectors, wherein generating each feature vector comprises convolving a respective feature with the test image;

generate a classified image by using the one or more feature vectors to apply an image classifier to the test image, the image classifier comprising at least one decision tree, wherein application of the image classifier to the test image comprises feeding the one or more feature vectors through the at least one decision tree to generate at least one pixel value of the test image, the classified image comprising a plurality of pixel values, wherein generation of each pixel value assigns the pixel value a probability that its associated pixel is related to an anatomical element; and evaluate the classified image using an anatomical model to detect at least one anatomical element within the classified image.

* * * * *